United States Patent [19]
Barten

[11] Patent Number: 5,917,128
[45] Date of Patent: Jun. 29, 1999

[54] CYTOPLASMIC MALE STERILE BRASSICA OLERACEA PLANT, AND METHOD FOR OBTAINING SUCH PLANT

[75] Inventor: Pieter Barten, Noord Schwarwoude, Netherlands

[73] Assignee: Bejo Zaden B.V., Warmenhuizen, Netherlands

[21] Appl. No.: 08/867,440

[22] Filed: Jun. 2, 1997

[30] Foreign Application Priority Data

May 31, 1996 [NL] Netherlands ............... 1003239

[51] Int. Cl.$^6$ .............. A01H 5/00; A01H 5/10; C12N 5/14; C12N 15/05
[52] U.S. Cl. ............ 800/303; 800/269; 800/274; 800/277; 800/304; 800/306; 435/419; 435/421; 435/453
[58] Field of Search ................ 800/205, 220, 800/255, DIG. 15–17, 269, 274, 277, 303, 304, 306; 435/172.2, 419, 421, 453

[56] References Cited

FOREIGN PATENT DOCUMENTS

| | | |
|---|---|---|
| 0255355 | 2/1988 | European Pat. Off. . |
| 9400518 | 2/1995 | Netherlands . |
| 2211205 | 6/1989 | United Kingdom . |
| 9205251 | 4/1992 | WIPO . |

OTHER PUBLICATIONS

Database WPI, Section Ch, Week 8941, Derwent Publications Ltd., London Class A97, AN89–296558 & JP 01218530A (Mitsubishi Kasei Corp).

TAG, Theoretical and Applied Genetics, 1992, vol. 83, pp. 313–320, "'Synthesis of Brassica Oleracea/Brassica Napus Somatic Hybrid Plants with Novel Organelle DNA Compositions", Kao et al.

Physiologia Plantarum, 1992, vol. 85, pp. 325–328, "Organelle Assortment and Mitochondrial DNA Rearrangements in Brassica Somatic Hybrids and Cyrids", Earle et al.

Plant Science, 1987, vol. 53, pp. 343–348, "The Transfer of Cytoplasmic Male Sterility to Winter–Type Oilseed Rape (Brassica Napus L.) by Protoplast Fusion", Barsby et al.

Singh et al. Plant Cell 3(12): 1349–1362, Dec. 1991.
Yarrow et al. Plant Cell Reports 9(4): 185–188, Aug. 1990.
Jourdan et al. Theor. Appl. Genet. 78(2): 271–279, 1989.

Primary Examiner—David T. Fox
Attorney, Agent, or Firm—Jones, Day, Reavis & Pogue

[57] ABSTRACT

B. oleracea plant, whose cytoplasm is provided, via protoplast fusion, with mitochondria comprising DNA at least partially originating from a B. napus plant, and which is linked to the property of cytoplasmic male sterility (CMS) (i.e. responsible for cytoplasmic male sterility in the B. oleracea plant), and whose cells are provided with species-specific nuclear genome being normal for this plant.

6 Claims, 1 Drawing Sheet

CYTOPLASMIC MALE STERILE BRASSICA OLERACEA PLANT, AND METHOD FOR OBTAINING SUCH PLANT

FIELD OF THE INVENTION

The invention relates to a cytoplasmic male sterile *Brassica oleracea* plant according to the main claim, i.e. to the development of new parent lines of such a plant. The invention furthermore relates to a method for obtaining said male sterile plant, as well as to hybrid seeds obtained from the new parent lines.

Brassica crops have been cultivated for centuries as food crops, while their seed content serves as a basis of various food products (vegetable oil, mustard etc.).

Since 1970 various Brassica vegetable crops have been sold as hybrid seeds. Such seeds give hybrid Brassica plants, which, being the crossing products of two strongly inbred parent lines, combine the genetic properties thereof. If either one or both parent lines are partly self-pollinating, measures have to be taken to prevent self-pollination in order to obtain pure hybrid Brassica plants. One anti self-pollination measure uses the so-called self incompatibility of one of both parent lines. In this way it is prevented that fertile pollen can grow in the pistil of specific plants, including the pistil of the pollen producing Brassica plant itself. A disadvantage of this method is that in some cases self-pollination still occurs. As a result the seed yield will have a high inbred percentage. Another measure to prevent self-pollination of either one of the parent lines is based on the use of cytoplasmic male sterility (CMS). In radish (*Raphanus sativus*) a cytoplasm has been found that induces male sterility, which cytoplasm is also known as Ogura CMS cytoplasm. Through protoplast fusion mitochondria of the Ogura CMS cytoplasm are introduced in *Brassica oleracea* plants, whereby the nucleus originates from normal fertile *Brassica oleracea* plants. In this way CMS *Brassica oleracea* plants are obtained. The chloroplasts in the Ogura CMS cytoplasm, which comprise DNA which is responsible for cold sensitivity of plants having this cytoplasm, have been removed through fusions.

SUMMARY OF THE INVENTION

The purpose of the invention is to obtain a cytoplasmic male sterile *Brassica oleracea* plant, in which the disadvantages of the prior art as mentioned before are overcome, and whereby an alternative is given for the Ogura CMS cytoplasm, and in order to achieve that purpose the cytoplasm of this plant is provided, by using protoplast fusion, with mitochondria comprising DNA which originates, at least partially so, from a *Brassica napus* plant and which is linked to (the property of) cytoplasmic male sterility, in other words, responsible for cytoplasmic male sterility in the *Brassica oleracea* plant. Extensive research has surprisingly shown that, despite the fact that *Brassica napus* plants are normal fertile, protoplast fusion can efficiently induce cytoplasmic male sterility in a *Brassica oleracea* plant by using the right mitochondrial DNA from a *Brassica nanus* plant. The aforementioned protoplast fusion is preferably carried out with leaf protoplasts from the *Brassica napus* plant (donor) on the one hand and with hypocotyl protoplasts from a *Brassica oleracca* plant (acceptor) on the other hand.

In a preferred embodiment according to the invention the cytoplasm of *Brassica oleracea* plant is furthermore provided with species-specific nuclear genome being normal for this plant. This makes it into a 100% pure product.

In another embodiment according to the invention the cells comprise species-specific mitochondria for *Brassica napus*.

In a further embodiment according to the invention the species-specific mitochondria are introduced through somatic hybridization. In cell fusion the nuclear coded genetic composition of a plant which receives cytoplasm remains unchanged (preferably in its entirety). A backcrossing programmed is not necessary, therefore, as cytoplasm having the desired composition is obtained in one go. In practice it has become apparent that *Brassica oleracea* plants obtained after protoplast fusion are often tetraploid or aneuploid. Ploidy levels may thereby increase to more than ten times C, with C being haploid genome. Plants with a non-diploid genome are characterized in that their growth is different and in that male as well as female sterility occurs. Application of flow cytometry removes all non-pure diploid plants from a population of *Brassica oleracea* plants obtained through fusion. Following this fusion the diploid plants are subject to molecular analysis; through this analysis it is determined which plants contain mitochondrial DNA (or a fragment thereof) which is known to be closely linked genetically to CMS.

In a further embodiment according to the invention *Brassica oleracea* plant is chosen from the group consisting of:

cauliflower (*Brassica oleracea* L. convar. botrytis (L.) Alef. var. botrytis L.), broccoli *Brassica oleracea* L. convar. botrytis (L.) Alef var. cymosa Duch.), Romanesco (*Brassica oleracea* L. convar. botrytis (L.) Alef. var. botrytis L.), Brussels sprouts (*Brassica oleracea* L. convar. oleracea var. gemnifera DC.), white cabbage (*Brassica oleracea* L. convar. capitata (L.) Alef. var. alba DC.), oxheart cabbage or pointed cabbage (*Brassica oleracea L.* convar. capitata (L.) Alef. var. alba DC.), red cabbage (*Brassica oleracea* L. convar. capitata (L.) Alef. var. rubra DC.), savoy cabbage (*Brassica oleracea L.* convar. capitata (L.) Alef. var. sabauda L.), Kohlrabi (*Brassica oleracea* L. convar. acephala (DC.) Alef. var. gongyloides), curly kale cabbage (*Brassica oleracea* L. convar. acephala (DC.) Alef. var. sabellica L.), portuguese cabbage (*Brassica oleracea* var. tronchuda syn. costata).

The invention also relates to seeds or plant parts from plants according to the invention.

The invention furthermore relates to a cell of a *Brassica oleracea* plant, the cytoplasm of which is provided, via protoplast fusion, with mitochondria comprising DNA at least partially originating from a *Brassica napus* plant, and which is linked to (the property of) cytoplasmic male sterility (CMS) (i.e. responsible for cytoplasmic male sterility in the *Brassica oleracea* plant). The hybrid cell comprises mitochondrial DNA being the carrier of cytoplasmic male sterility (CMS).

The invention also relates to a process for producing a *Brassica oleracea* plant comprising the step of providing, via protoplast fusion, the cytoplasm thereof with mitochondria having DNA at least partially originating from a *Brassica napus* plant, and which is linked to (the property of) cytoplasmic male sterility (CMS) (i.e. responsible for cytoplasmic male sterility in the *Brassica oleracea* plant).

Seeds from both a *Brassica napus* plant (donor) and a *Brassica oleracea* plant (acceptor) are sterilized and germinated on MS30 medium or the like; for the donor this is carried out in the light, plants are kept through cutting shoots and placing them on fresh growth medium. Seeds from the acceptor are germinated in the dark; from the etiolated plantlets obtained the hypocotyl is used. Protoplasts are isolated by treating leaf and/or hypocotyl material with cell wall-degrading enzymes such as pectinase and cellulase after pre plasmolysis; this takes place in a plasmolyzing solution. After filtration and centrifugation, protoplasts from the donor are gamma-irradiated with gamma irradiation. Protoplasts from the acceptor are treated with IOA, after which both protoplast groups are fused. During fusion PEG agent is used to enhance agglutination; high pH during fusion is essential. During fusion protoplasts are left undisturbed in order not to interfere with the fusion process. After fusion the PEG solution is washed out and replaced by a regeneration medium. Regeneration of the protoplasts takes place in this medium, whereby the presence of sugars such as sucrose and hormones like 2,4-D, BA and NAA and the like is of decisive importance. During regeneration the osmotic value of the regeneration medium is gradually reduced by repeatedly adding medium having a lowered sucrose concentration. Micro calli being developed are transferred to solid regeneration medium. Every fortnight said calli are transferred to fresh regeneration medium. Newly developed shoots are placed on rooting medium, in which rooting is enhanced by a phytohormone like IAA. Regenerated plants are examined for their ploidy level by taking leaf samples and determining the relative DNA content of the nuclei with a flow cytometer. Plants containing the pure diploid genome are kept, the other plants are discarded. The remaining plants are analyzed further by means of molecular techniques Using DNA isolated from leaf samples and a probe specifically for mitochondrial DNA, it is investigated whether the right mitochondria are present in the plants. Plants comprising the cytoplasm from the acceptor (to be regarded as escapees) are destroyed. The remaining plants are reproduced by crossing and investigated for usability under glasshouse and field conditions. Characteristics such as sterility, seed yield and plant quality receive special attention thereby.

DETAILED DESCRIPTION OF THE DRAWINGS

Figure 1:
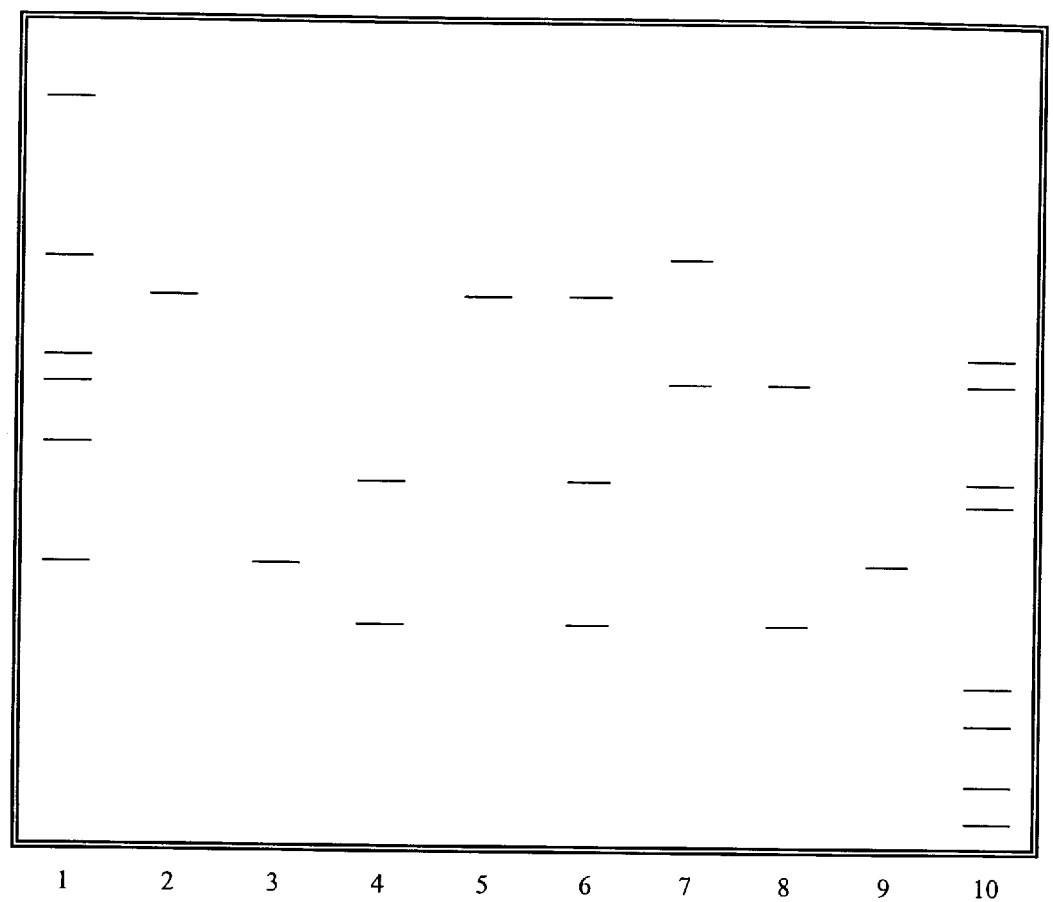
FIG. 1 presents a luminescogramme with cytoplasm from *B. oleracea, B. napus* as fertile donor, *B. oleracea* with the ogura cytoplasm, *B. campestris* with the anand cytoplasm, *B. napus* with the polima cytoplasm and *B. oleracea* with mitochondria from the fertile *B. napus*.

In FIG. 1, hybridization is carried out with a DNA probe. This probe consists of a mitochondrial DNA fragment isolated from plants that are phenotypically sterile (CMS) and after digestion with EcoRI cloned in Escherichia coli. The band is characterized in that it can be cut from the *E. coli* plasmid DNA with EcoRI and hybridizes in a characterizing way with mitochondrial DNA from cabbage. In FIG. 1, the description of the various lanes are as follows:

lane 1: molecular weight markers, from top to bottom: 21226 bp, 7421 bp, 5804 bp, 5643 bp, 4878 bp, 3530 bp (λ DNA :: EcoRI; Boehringer Mannheim)

lane 2: fertile *B. napus* as donor lane 3: *B. oleracea* with ogura lane 4: *B. oleracea* as acceptor; the upper band may be absent in some cases, depending on the stringency of the washing steps lane 5: *B. oleracea* plant with CMS which is created from fusion with the pattern of the donor in lane 2.

lane 6: *B. oleracea* plant with CMS which is created from fusion with a combined pattern from the donor as in lane 2 and the acceptor in lane 4. Such a plant is sterile and is also indicated to have the CMS property, therefore.

lane 7: *B. campestris* with anand cytoplasm (from *B. juncea* background)

lane 8: *B. napus* with polima cytoplasm lane 9: *B. oleracea* with ogura cytoplasm (=lane 3)

lane 10: molecular weight markers, from top to bottom: 5148 bp, 4g37 bp, 4268 bp, 3530 bp, 2c27 bp, 1g04 bp, 1584 bp, 1375 bp, (λ DNA :: EcoRI and HindIII, Boehringer Mannheim)

DETAILED DESCRIPTION OF THE INVENTION

The invention will be further elucidated with reference to the following examples, which are all preferred embodiments of the invention.

EXAMPLE 1

Surface sterilization of seed.

Seeds from cabbage (*Brassica oleracea*) are packed in filtration paper and submerged in a mixture containing 70% ethanol/30% water for 10 seconds; followed by submersion in sterile water of 55° C. for 5 minutes. This treatment is followed by another treatment with 0.3% (w/v) NaOCl+Tween80 for 20 minutes; this treatment takes place in a laminar flow cabinet.

After this treatment the seed package is washed 3 times with sterile water, for 5, 5 and 10 minutes respectively.

EXAMPLE 2

Sowing of parent (starting) material for hypocotyl protoplasts.

After a final washing step the seed package is opened and placed on ½MS15 medium in a container. The containers are kept in the dark at a temperature of 25° C. After about 7 days hypocotyls can be used for protoplast isolation.

EXAMPLE 3

Sowing of parent (starting) material for leaf protoplasts.

The sterilized seeds are sown according to Example 2. The containers are placed in the light at 25° C. After 14–28 days plant leafs can be used for protoplast isolation; shoot tips of the plants are placed on fresh BB; the containers are stored at 25° C. in the light. The fully expanded leaves are used for protoplast isolation.

EXAMPLE 4

Protoplast isolation.

Leaf and hypocotyl material is cut into small pieces and placed in glass petri dishes (⌀ 11 cm) or TC-quality petri dishes (⌀ 9 cm) containing a thin layer (12 ml) of plasmolyzing solution. After said cutting another 12 ml of plasmolyzing solution is added.

The petri dishes are wrapped in aluminum foil and stored in a laminar flow cabinet for at least one hour.

After said one hour the plasmolyzing solution is replaced by approximately 24 ml of fresh enzyme solution.

The whole is stored overnight in aluminum foil at 25° C.; the enzyme mixture for obtaining hypocotyl protoplasts is placed on a shaker, the enzyme for leaf protoplasts, however, is not. The shaker is set to 30 rpm, with an amplitude of 15 mm.

After incubation the suspensions are filtered over a Teflon filter holder with two nylon filters of 110 μm and 53 μm respectively. The filters are re-rinsed with ⅓ volume of CPW16 (±8 ml).

The suspensions are centrifuged at 110×g for 5 minutes.

The bands that have been formed, which contain the protoplasts, are sucked up with a sterile pasteur pipette and transferred to a new centrifuge tube. After carefully adding 9 ml of W5 the protoplast suspensions are centrifuged at 75×g for 5 minutes.

The leaf protoplasts are further treated as follows: the supernatant of the various centrifuge tubes is poured off and the pellets are carefully resuspended in 1–2 ml of W5. The contents of the different centrifuge tubes are combined, and W5 is added to a total of 10 ml.

The centrifuge tube containing the protoplasts (donor) is sealed with Parafilm, wrapped in aluminum foil and placed on ice until radiation with 50 kRad takes place.

The hypocotyl protoplasts are treated as follows: the supernatant of the various centrifuge tubes is poured off and the pellets are carefully resuspended in 1–2 ml of W5±2 mM IOA (4° C.). The contents of the different centrifuge tubes are combined and supplemented to a total of 10 ml with W5±2mMIOA, and subsequently incubated in a refrigerator at 4° C. for 10 minutes.

After this the suspension is centrifuged at 75×g for 5 minutes (the total incubation time in the IOA is 15 minutes, therefore).

The pellet is resuspended in 1–2 ml of W5 and the suspension is supplemented with W5 to a total of 10 ml, after which the whole is transferred to a sterile 50 ml flask. This flask, wrapped in aluminum foil, is incubated at 25° C. on a shaker (approx. 30 rpm; amplitude 15 mm) during the time that the protoplasts are irradiated. After this the contents of the flask are transferred to a centrifuge tube.

The two tubes with both leaf and hypocotyl protoplasts are centrifuged at 75×g for 5 minutes, after which the pellet is resuspended in 1–3 ml of W5.

The density of the protoplast suspensions is determined with a haemocytometer.

EXAMPLE 5
Protoplast fusion.

The protoplasts of both suspensions are combined to a final density of $9.10^5$ protoplasts/ml for fusion.

40 μl drops are transferred to petri dishes with a micro litre pipette:

11 40 μl drops in a ⊕ 6 cm petri dish or 25 40 μl drops in a ⊕ 9 cm petri dish.

The lid is placed on the dishes, after which light is switched off and the laminar flow cabinet is turned off for 15 minutes to enable the protoplasts to adhere to the bottom of the petri dishes.

The laminar flow cabinet is switched on again and 60 μl of PEG-solution is added to each drop of protoplasts.

After 3–5 minutes the following quantity of SV I is added to the petri dishes:

4 ml to a ⊕ 6 cm dish
9 ml to a ⊕ 9 cm dish

After 3–5 minutes the solution is sucked up and SV II is added:

4 ml to a ⊕ 6 cm dish
9 ml to a ⊕ 9 cm dish

After 3–5 minutes the solution is sucked and 8p is carefully added:

4 ml in a ⊕ 6 cm dish
9 ml in a ⊕ 9 cm dish

It is important to add 8p medium carefully, in order to prevent the protoplasts from releasing from the bottom of the petri dish too early.

After 3–5 minutes the 8p medium is sucked up and new 8p medium is added. Now protoplasts can release themselves from the bottom of the petri dishes:

4 ml in a 6 cm dish
9 ml in a 9 cm dish

The petri dishes are sealed with Paraflim and stored in light of approximately 500 lux.

EXAMPLE 6
Regeneration.

On day 8 after fusion 8pA is added to the petri dishes in an amount of up to three times the original volume, that is:

8 ml to a ⊕ 6 cm dish
18ml to a ⊕ 9 cm dish

The petri dishes are placed in the light.

On day 15 after fusion the micro calli that have developed on the bottom of the dishes are carefully scraped off with a sterile spatula. The contents of the petri dish are distributed over four centrifuge tubes with a 10 ml pipette and centrifuged at 75×g for 5 minutes. Meanwhile 6 ml of K,PPS-V medium is pipetted into four new petri dishes. After centrifuging the supernatant is poured off and the 6 ml of K,3PPS-V medium is added to the pellet. The pellet consists of dividing cells and micro calli and can easily be resuspended in the K,PPS-V medium. The medium and the pellet are sucked up with a 10 ml pipette and pipetted into the petri dishes. From day 21 after fusion the micro calli that have developed are inoculated from the K,PPS-V medium to K,PPS-R medium. The growing (micro) calli are transferred to fresh K,PPS-R medium every 2 weeks.

As soon as the calli exhibit shoot development they are transferred to containers with K,PPS-R medium. As soon as the shoots are big enough, they are harvested and placed in a rooting medium (BB medium).

EXAMPLE 7
Flow cytrometric determinations.

Leaf samples of ±1 cm2 of a plant that is to be analyzed are taken and placed in 2 ml of DAPI solution. This sample is cut into small pieces with a sharp razor blade and filtered through a 15 μm filter. The sample is measured with a Partec CA-II cell analyzer according to the De Laat et al. method. The relative DNA content of the plants is determined by comparing the peak positions of the fusion plants with those of diploid plants.

EXAMPLE 8
Molecular determinations.

*Brassica oleracea* plants with cytoplasmic male sterility obtained through somatic hybridization are distinguished from *Brassica oleracea* plants with different cytoplasm (different cabbage species including those with ogura, anand or polima cytoplasm) with a DNA probe. This probe consists of a mitochondrial DNA fragment isolated from plants that are phenotypically sterile (CMS) and after digestion with EcoRI cloned in *Escherichia coli*. The band is characterized in that it can be cut from the *E. coli* plasmid DNA with EcoRI and hybridizes in a characterizing way with mitochondrial DNA from cabbage (see figure).

200 mg of leaf material from the plants that are to be analyzed is collected in a reaction tube and frozen with liquid nitrogen. To these tubes 750 μl of extraction buffer is added and homogenized with a Potterstick. The sample is centrifuged for 10 minutes at 13000×g and the supernatant including the green material is carefully poured off. 125 μl of extraction buffer is added to the pellet, after resuspension 135 μl of lysis buffer and 60 μl of lauryl sarcosine solution is added. After briefly mixing the mixture is heated to 65° C. for 20 minutes. 375 μl of chloroform/isoamyl alcohol is added and the reaction tube is shaken at least 40 times. Centrifuge for 10 minutes at 13000×g, transfer the upper fraction to a new reaction vessel and repeat the CHCl$_3$/IAA step one more time if necessary. Finally, add 500 μl of isopropanol and shake the reaction tubes a few times. Centrifuge for 5 minutes at 13000×g. The pellet is resuspended in 500 μl of TE buffer.

Digestion of DNA with restriction-endonuclease is carried out as follows: approximately 4 μg DNA is necessary for RFLP analysis. The final solution in which restriction takes place consists of 0.1 volume universal cut-buffer like One-Phor-All Buffer PLUS (Pharmacia), 4 μg DNA, 4 mM spermidine and 2 units restriction enzyme. Incubation takes place at 37° C. for at least 3 hours.

The reaction is stopped by changing the EDTA concentration to 10 mM from a stock solution. The DNA is precipitated by adding 0.1 volume of 3M NaAc and 2.5 volume ethanol of −20° C. The mixture is kept at −20° C. for 2 hours; after centrifugation for 10 minutes at 10000×g the pellet is washed with ice-cold 70% ethanol/water, dried and solved in TE buffer.

Agarose gel electrophoresis of the DNA fragments that are to be separated is carried out as follows: 2 g agarose is weighed and boiled in 250 ml of TAE buffer. After cooling to a lukewarm temperature ehtidium bromide is added to a final concentration of 0.5 mg/1. The gel is poured and cooled down until it is set. The samples are applied to loading buffer and DNA fragments are separated. Electrophoresis is stopped when the front marker BPF has come to approximately 1 cm from the top of the gel.

In preparation to blotting, the gel is treated as follows.

5 minutes in 0.25M HCl (1×)

15 minutes in 0.5M NaOH/1.5M NaCl (2×)

10 minutes in 1M NH$_4$Ac/20 mM NaOH (2×)

A Hybond membrane (Amersham) is cut to the same size as the gel and wetted by immersion in 2×SSC for a few seconds and thereafter in 1M NH$_4$Ac/20 mM NaOH. Three pieces of Whatman 3 MM filtration paper are cut to this size. A setup is made in which the DNA is transferred from the gel to the membrane through liquid transport for 4 hours. The transfer takes place in 1M NH$_4$Ac/20 mM NaOH. After drying of the membrane, the DNA is cross-linked to the membrane by radiation with UV light for one minute on both sides.

The required DNA probe is labelled as follows: the transferred DNA is denaturated by heating at 95° C. for 10 minutes and quick cooling down on ice. The following is mixed in a reaction vessel:

10 ng-3 μg of DNA

2 μl of hexanucelotide mixture

2 μl of dNTP's (with digoxigenine-dUTP)

1 μl of Klenow polymerase

After mixing, incubation overnight follows at 37° C. DNA is precipitated by adding 2 μl of 3M NaAc and 44 μl of ethanol (96%). The mixture is placed at −20° C. for 30 minutes. After centrifugation at 10000×g for 15 minutes, the pellet is washed with 70% ethanol in water (v/v) and the dried pellet is dissolved in 50 μl of TE.

Hybridization of the labelled fragments to the membrane:

The membrane is placed in 2×SSC for a few seconds. Then the membrane is sealed in a bag with 20 ml of prehybridisation mixture. The membrane is incubated for at least one hour at 60–65° C. The prehybridisation mixture is removed and replaced by 4 ml of hybridisation mixture and incubated overnight. After incubation the membrane is washed: 4 times in washing solution 1 for 2 minutes; 4 times in washing solution 2 for 2 minutes, and 2 times in washing solution 3 (at 60–65° C.) for 15 minutes.

Detection of the labelled bands takes place at room temperature, the blot is rinsed in rinsing buffer 1 and then sealed with 10 ml of rinsing buffer 2 per 100 cm$^2$ of membrane. After incubation on a shaker for 30 minutes, rinsing buffer 2 is replaced by 15 ml of anti-dig solution per 100 cm$^2$ of membrane. After incubation on a shaker for 30 minutes, the membrane is washed: 2 to 3 times in rinsing buffer 2 for 10 minutes; 3 to 4 times in rinsing buffer 1 for 10 minutes, and once in rinsing buffer 3. The membrane is incubated with 10 ml of AMPPD solution per 100 cm$^2$ of membrane for 20 minutes. The membrane is placed in a cassette with a Polaroid film on top; after sufficient exposure the film is removed and developed.

EXAMPLE 9

Description of floral phenotype of a cytoplasmic male sterile *Brassica oleracea* with mitochondria from *Brassica napus*.

Inflorescence: main axis of the bunch towards the top, sometimes shortened or fasciated into bundles, often branched. Bracts seldom present, sometimes turned and rolled. Petioles sometimes shortened or fasciated into bundles.

Flower bud: often closed, sometimes open, the sides of the sepals not touching each other and being folded. Smooth to bulged surface, top mostly rolled-in, sometimes pointed. Pistil often outgrows the top.

Flower: sepals 1–4 mm wide, 4–12 mm long, upright, often slightly turning, sides sometimes bent inwardly, top bent inwardly. Nectaries present. Petals 4, sometimes up to a manifold of this up to 40; 4–7 mm wide, 11–19 mm long. At a multitude of 4 the inner petals are often much shorter. Claw may seemingly be fasciated to a tube. Plate mainly not bent backwards, often strongly rolled sideways, sometimes strongly turned. Color upper side white or yellow RHS 2A-3A-2C-3C-4A-5A-5B-6A, bottom side white or yellow RHS 2A-2B-2C-3A-3C-4B-4C-4A, side of top often smooth, sometimes notched. Stamina 6 to 2, and in that case sometimes fasciated 2 by 2, length up to half the sepals, sometimes the same length as the sepals. Anthers, small and triangular, pollen not present. One pistil, sometimes as many as three, one being longer than the others, mainly upright, without pollination often growing to a length of about 30 mm. Bill and pistil sometimes curved, sometimes slightly swollen. Ovary often turning and rolled.

Flower in the top of the bunch sometimes almost without sepals, petals and stamina and with strongly turning and rolled ovaries, or seemingly faciated 2 by 2; split open along a fascination seam, resembling leaf on bract with parallel nervature.

|  | CPW16 | W5 | preplasmolysis | plasmolysis | K3PPS-1 | K3PPS-V | K3PPS-R | 8P | 8PA | ½MS15 | MS30 | BB |
|---|---|---|---|---|---|---|---|---|---|---|---|---|
| KNO₃ (mM) | 10 | — | — | — | 24.73 | 24.73 | 24.73 | 18.80 | 18.80 | 9.40 | 18.79 | 18.79 |
| NH₄NO₃ (mM) | — | — | — | — | 3.13 | 3.13 | 3.13 | 7.49 | 7.49 | 10.3 | 20.61 | 20.61 |
| FeNaEDTA (mM) | — | — | — | — | 0.10 | 0.10 | 0.10 | 0.10 | 0.10 | 0.10 | 0.10 | 0.20 |
| MgSO₄.7H₂O (mM) | 1.0 | — | — | — | 1.01 | 1.01 | 1.01 | 1.22 | 1.22 | 0.75 | 1.50 | 1.50 |
| CaCl₂ (mM) | 10 | 125 | 50 | 50 | 2.00 | 2.00 | 2.00 | 4.08 | 4.08 | 1.50 | 2.99 | 2.99 |
| KCl (mM) | — | 10.7 | — | — | — | — | — | 4 | 4 | — | — | — |
| NaCl (mM) | — | 154 | — | — | — | — | — | — | — | — | — | — |
| KH₂PO₄ (mM) | 0.2 | — | — | — | — | — | — | 1.25 | 1.25 | 0.63 | 1.25 | 1.25 |
| NaH₂PO₄ (mM) | — | — | — | — | 1.09 | 1.09 | 1.09 | — | — | — | — | — |
| (NH₄)₂SO₄ (mM) | — | — | — | — | 1.01 | 1.01 | 1.01 | — | — | — | — | — |
| H₃BO₃ (μM) | — | — | — | — | 48.52 | 48.52 | 48.52 | 48.52 | 48.52 | 0.10 | 0.10 | 0.10 |
| CuSO₄.5H₂O (μM) | 0.10 | — | — | — | 0.10 | 0.10 | 0.10 | 0.10 | 0.10 | 0.10 | 0.10 | 0.10 |
| MnSO₄.H₂O (μM) | — | — | — | — | 59.16 | 59.16 | 59.16 | 59.16 | 59.16 | 0.10 | 0.10 | 0.10 |
| KI (μM) | .97 | — | — | — | 6.00 | 6.00 | 6.00 | 4.52 | 4.52 | 5.00 | 5.00 | 5.00 |
| Na₂MoO₄.2H₂O (μM) | — | — | — | — | 1.03 | 1.03 | 1.03 | 1.03 | 1.03 | 1.03 | 1.03 | 1.03 |
| ZnSO₄.7H₂O (μM) | — | — | — | — | 6.96 | 6.96 | 6.96 | 6.96 | 6.96 | 29.91 | 29.91 | 29.91 |
| CoCl₂.6H₂O (μM) | — | — | — | — | 0.11 | 0.11 | 0.11 | 0.11 | 0.11 | 0.11 | 0.11 | 0.11 |
| glycine (μM) | — | — | — | — | — | — | — | — | — | 26.64 | 26.64 | 26.64 |
| myo-inositol (μM) | — | — | — | — | 0.56 | 0.56 | 0.56 | 0.56 | 0.56 | 0.56 | 0.56 | 0.56 |
| pyridoxine HCl (μM) | — | — | — | — | 4.86 | 4.86 | 4.86 | 4.86 | 4.86 | 2.43 | 2.43 | 2.43 |
| thiamine HCl (μM) | — | — | — | — | 29.65 | 29.65 | 29.65 | 29.65 | 29.65 | 0.30 | 0.30 | 0.30 |
| nicotinic acid (μM) | — | — | — | — | 8.12 | 8.12 | 8.12 | 8.12 | 8.12 | 4.06 | 4.06 | 4.06 |
| Na-pyruvate (μM) | — | — | — | — | — | — | — | 181 | 181 | — | — | — |
| citric acid (μM) | — | — | — | — | — | — | — | 208 | 208 | — | — | — |
| malic acid (μM) | — | — | — | — | — | — | — | 298 | 298 | — | — | — |
| fumaric acid (μM) | — | — | — | — | — | — | — | 344 | 344 | — | — | — |
| ascorbic acid (μM) | — | — | — | — | — | — | — | 5.7 | 5.7 | — | — | — |
| glucose (mM) | — | 5.55 | — | — | — | — | — | 379 | 379 | — | — | — |
| fructose (mM) | — | — | — | — | — | — | — | 1.39 | 1.39 | — | — | — |
| ribose (mM) | — | — | — | — | — | — | — | 1.67 | 1.67 | — | — | — |
| manitose (mM) | — | — | — | — | — | — | — | 1.39 | 1.39 | — | — | — |
| rbamnose (mM) | — | — | — | — | — | — | — | 1.52 | 1.52 | — | — | — |
| cellobiose (mM) | — | — | — | — | — | — | — | 0.73 | 0.73 | — | — | — |
| sorbitol (mM) | — | — | 50 | 300 | — | — | — | 1.37 | 1.37 | — | — | — |
| mannitol (mM) | — | — | — | — | — | — | — | 1.37 | 1.37 | — | — | — |
| caseinehydrolysate (mg/l) | — | — | — | — | — | — | — | 250 | 250 | — | — | — |
| sucrose (mM) | 467 | — | — | — | 400 | 100 | 30 | 0.73 | 0.73 | 43.82 | 43.82 | 43.82 |
| xylose (mM) | — | — | — | — | 1.67 | 1.67 | 1.67 | 1.67 | 1.67 | — | — | — |
| coconut milk (mM) | — | — | — | — | — | — | — | 20 | 20 | — | — | — |
| 2,4-D (μM) | — | — | — | — | 0.45 | 0.45 | — | 4.5 | — | — | — | — |
| BA (μM) | — | — | — | — | 4.4 | 4.4 | 2.2 | 2.2 | — | — | — | — |
| NAA (μM) | — | — | — | — | 0.13 | 0.13 | — | 0.49 | — | — | — | — |
| IAA (μM) | — | — | — | — | — | — | 0.57 | — | — | — | — | 5.71 |
| zeatin (μM) | — | — | — | — | — | — | 2.28 | — | — | — | — | — |
| agarose (% (w/v)) | — | — | — | — | — | 0.4 | — | — | — | — | — | — |
| agar (% (w/v)) | — | — | — | — | — | — | 0.7 | — | — | 0.7 | 0.7 | 0.7 |
| pH (temp. comp) | ambient | 5.6 | 7.0 | 6.4 | 5.6 | 5.6 | 5.6 | 5.6 | 5.6 | 5.8 | 5.8 | 6.0 |

Further Solutions for Cell Biology enzyme solution
  1% (w/v) cellulase R-10 in K3PPS-I
  0.1% (w/v) pectinase in K₃PPS-I
  pH=5.6
PEG solution
  PEG1500 266.7 mM
  glucose 300 mM
  CaCl₂. 2H₂O 50 mM
  pH=7.0
SV I
  50 ml of PEG solution+100 ml of Pre-plasmolyzing solution
SV II
  20 ml of PEG solution+100 ml of Pre-plasmolyzing solution
IOA (iodacetamide)
  2 mM IOA in W₅; pH=5.6
  1% agarose solution in MilliQ water.

Solutions for Molecular Biology extraction buffer
  350 mM of sorbitol
  100 mM of Tris-base
  5 mM of EDTA
  add fresh: 20 mM of Na-bisulpbite lysisbuffer;
  20 mM of Tris-base
  50 mM of EDTA
  2M NaCl
  2% (w/v) CTAB
  N-lauryl sarcosine, Na salt: 10% (w/v)
  chloroform/isoamyl alcohol: 24:1 (v:v)
  isopropanol
TE: 10 mM of Tris-HCl; pH 8.0
  1 mM of EDTA
  4 mM of spermidine
EDTA stock solution 1M
  3M of NaAc
  ethanol 96%
  70% ethanol/water v/v
  ethidiumbromide solution: 10 mg/ml of H₂O
TAE buffer
  4.84 gram Tris base/l 1.14 ml of acetic acid
10 mM of EDTA; pH 8.0
loading buffer
  24% Ficoll 400
  0.1% SDS
  0.1% xylenecyanole
  0.1% brome phenole blue
  0.25M HCl
  0.5M NaOH/1.5M NaCl
  1M NH₄Ac/20 mM of NaOH
2×SSC:
  30 mM of Na-citrate.2H₂O; pH 7.2
  300mM of NaCl
0.2 SSC: 10×diluted 2×SSC
0.1×SSC: 20×diluted 2×SSC
hexanucleotide mix: 10×concentrated hexanucleotide mix from Boehringer Mannheim
dNTP:
  0.1 mM of dATP
  0.1 mM of dCTP
  0.1 mM of dGTP
  0.65 mM of dTTP
  0.35 mM of digoxygenine-dUTP (Boehringer)
blocking reagent: Boehringer Mannheim; art.#1175041 pre-hybridisation mix
  75 mM of Na-citrate
  750 mM of NaCl
  0.5% blocking reagent
  0.1% N-lauroyl sarcosine (w/v)
  10 0.2% SDS
hybridisation mix
  75 mM of Na-citraat
  750 mM of NaCl
  0.5% blocking reagent
  0.1% N-lauroylsarcosine
  0.2% SDS
  40–50 ng digoxygenine-dUTP labelled probe/ml
washing solution 1: 2×SSC+0.1% (w/v) SDS
washing solution 2: 0.2×SSC+0.1% (w/v) SDS
washing solution 3: 0.1×SSC+0.1% (w/v) SDS
rinsing buffer 1
  100 mM of Tris-HCl pH 7.5
  150 mM of NaCl
rinsing buffer 2
  rinsing buffer 1
  0.5% blocking agens (freshly prepared)
rinsing buffer 3
  rinsing buffer 1
  50 mM of MgCl₂
anti-dig-AP conjugate: Boehringer Mannheim; art.nr 1175041
AMPPD Solution: 10 μl of AMPPD per ml of rinsing buffer 3 (0.26 μM)
Used abbreviations
  2.4D: 2.4-dichlorophenoxy acetic acid
  AMPPD: disodium 3-(4-methoxyspiro{1.2-dioxetane-3.2'-tricyclo-[3.3.1.1$^{3,7}$]decan}-4yl)phyenyl phosphate
  AP: acid fosfatase
  BA: 6-benzylaminopurine
  BPB bromophenolblue
  CMS: cyroplasmic male sterility
  DIG: digoxygenine
  dATP: desoxyadenosine triphosphate
  dCTP: desoxycytosine triphosphate
  dGTP: desoxyguanie triphosphate
  DNTP: desoxynucleotide triphosphate
  dTTP: desoxythyminetri phosphate
  DUTP: desoxyuracyl triphosphate
  EDTA: ethylenediaminetetra acetic acid
  g: acceleration of gravity (9.8 m.sec$^{-2}$)
  IOA: iodacetamide
  kRad:
  1000 Rad, unit of ionizing radiation
  μg: microgram
  μl: microliter
  mM: millimolar
  μm: micromolar
  M: molar
  MS: Murashige & Skoog
  NAA: naftalene acetic acid
  PEG: polyethylene glycol
  pH: measure of acidity
  rpm: revolutions per minute
  SSC: saline sodium citrate
  SDS: sodiumdodecyl sulphate
  TC: tissue culture
  UV: ultraviolet
  v/v: volume/volume
  w/v: weight/volume For almost all treatments it can be stated within which limits a pH, a concentration etc. has to be kept and at what level the experiments have to be carried out in practice. The three levels for these solutions/treatments are given below:
tissue culture media
  ½MS15, MS30 en BB:
    sugar e.g. sucrosis; concentration 0.5–600 mM, normally 200–400 mM.
    pH 5–10; normal 5.5–6.0. temperature cultivation: 22–27° C., normally 25° C. radiation: 0–60 kRad; normally 50 kRad. fusion temperature: 20–25° C.; usually 22° C. concentrations of plant hormones: 0–10 μM; normally 0–3 μM.

I claim:

1. A *Brassica oleracea* plant whose cellular cytoplasm is provided, via protoplast fusion and somatic hybridization, with mitochondrial DNA from a fertile *Brassica napus* plant, said DNA in combination with *Brassica oleracea*-specific nuclear DNA causing cytoplasmic male sterility in the *Brassica oleracea* plant.

2. The *Brassica oleracea* plant according to claim 1, selected from the group consisting of cauliflower (*Brassica oleracea* L. convar. *botrytis* (L.) Alef. var. *botrytis* L.), broccoli(*Brassica oleracea* L. convar. *botrytis* (L.) Alef var. *cymosa* Duch.), Romanesco (*Brassica oleracea* L. convar. *botrytis* (L.) Alef. var. *botrytis* L.), Brussels sprouts (*Brassica oleracea* L. convar. *oleracea* var. *gemnifera* DC.), white cabbage (*Brassica oleracea* L. convar. *capitata* (L.) Alef. var. *alba* DC.), oxheart cabbage or pointed cabbage (*Brassica oleracea* L. convar. *capitata* (L.) Alef. var. *alba*

DC.), red cabbage (*Brassica oleracea L. convar. capitata* (L.) *Alef.* var. *rubra* DC.). savoy cabbage (*Brassica oleracea L. convar. capitata* (L.) *Alef.* var. *sabauda* L.), kohlrabi (*Brassica oleracea L. convar. acephala* (DC.) *Alef.* var. *gongyloides*). curly kale cabbage (*Brassica oleracea L. convar. acephala* (DC.) *Alef.* var. *sabellica* L.), and portuguese cabbage (*Brassica oleracea* var. *tronchuda* syn. *costata*).

3. Seeds or plant parts from a *Brassica oleracea* plant whose cellular cytoplasm is provided, via protoplast fusion and somatic hybridization, with mitochondrial DNA from a fertile *Brassica napus* plant, said DNA in combination with *Brassica oleracea*-specific nuclear DNA causing cytoplasmic male sterility in the *Brassica oleracea* plant.

4. The seeds or plant parts according to claim 3, selected from the group consisting of cauliflower (*Brassica oleracea L. convar. botrytis* (L.) *Alef.* var. *botrytis* L.). broccoli (*Brassica oleracea L. convar. botrytis* (L.) *Alef* var. *cymosa* Duch.), Romanesco (*Brassica oleracea L. convar. botrytis* (L.) *Alef.* var. *botrytis* L.). Brussels sprouts (*Brassica oleracea L. convar. oleracea* var. *gemnifera* DC.). white cabbage (*Brassica oleracea L. convar. capitata* (L.) *Alef.* var. *alba* DC.). oxheart cabbage or pointed cabbage (]*Brassica oleracea L. convar. capitata* (L.) *Alef.* var. *alba* DC.). red cabbage (*Brassica oleracea L. convar. capitata* (L.) *Alef.* var. *rubra* DC.), savoy cabbage (*Brassica oleracea L. convar. capitata* (L.) *Alef.* var. *sabauda* L.). kohlrabi (*Brassica oleracea L. convar. acephala* (DC.) *Alef.* var. *gongyloides*). curly kale cabbage (*Brassica oleracea L. convar. acephala* (DC.) *Alef.* var. *sabellica* L.), and Portuguese cabbage (*Brassica oleracea* var. *tronchuda* syn. *costata*).

5. A cell of a *Brassica oleracea* plant, the cytoplasm of which is provided, via protoplast fusion and somatic hybridization, with mitochondrial DNA from a fertile *Brassica napus* plant, said DNA in combination with *Brassica oleracea*-specific nuclear DNA causing cytoplasmic male sterility in the *Brassica oleracea* plant.

6. A process for producing a *Brassica oleracea* plant comprising the step of providing, via protoplast fusion and somatic hybridization, cellular cytoplasm comprising mitochondrial DNA from a fertile *Brassica napus* plant, said DNA in combination with *Brassica oleracea*-specific nuclear DNA causing cytoplasmic male sterility in the *Brassica oleracea* plant.

* * * * *